United States Patent
Hu et al.

(10) Patent No.: US 7,039,723 B2
(45) Date of Patent: May 2, 2006

(54) ON-LINE IMAGE PROCESSING AND COMMUNICATION SYSTEM

(75) Inventors: Hui Hu, Waukesha, WI (US); Yi Sun, Brookfield, WI (US)

(73) Assignee: HInnovation, Inc., Wauwatosa, WI (US)

( * ) Notice: Subject to any disclaimer, the term of this patent is extended or adjusted under 35 U.S.C. 154(b) by 666 days.

(21) Appl. No.: 09/945,479

(22) Filed: Aug. 31, 2001

(65) Prior Publication Data

US 2003/0055896 A1    Mar. 20, 2003

(51) Int. Cl.
*G06F 15/16*    (2006.01)

(52) U.S. Cl. ..................................... 709/248

(58) Field of Classification Search ........ 709/201–203, 709/213, 217–219, 230–232, 246, 248, 214; 345/418–419, 581, 660
See application file for complete search history.

(56) References Cited

U.S. PATENT DOCUMENTS

| | | |
|---|---|---|
| 4,222,076 A | 9/1980 | Knowlton et al. |
| 4,475,104 A | 10/1984 | Shen |
| 4,625,289 A | 11/1986 | Rockwood |
| 4,737,921 A | 4/1988 | Goldwasser et al. |
| 4,748,511 A | 5/1988 | Nicols et al. |
| 4,910,609 A | 3/1990 | Nicholas et al. |
| 4,985,856 A | 1/1991 | Kaufman et al. |
| 4,987,554 A | 1/1991 | Kaufman |
| 5,005,126 A | 4/1991 | Haskin |
| 5,027,110 A | 6/1991 | Chang et al. |
| 5,038,302 A | 8/1991 | Kaufman |
| 5,101,475 A | 3/1992 | Kaufman et al. |
| 5,235,510 A | 8/1993 | Yamada et al. |
| 5,291,401 A | 3/1994 | Robinson |
| 5,297,034 A | 3/1994 | Weinstein |
| 5,321,520 A | 6/1994 | Inga et al. |
| 5,339,812 A | 8/1994 | Hardy et al. |
| 5,360,971 A | 11/1994 | Kaufman et al. |
| 5,408,249 A | 4/1995 | Wharton et al. |

(Continued)

FOREIGN PATENT DOCUMENTS

EP        0903694 A1    3/1999

(Continued)

OTHER PUBLICATIONS

"2D and 3D Progressive Transmission Using Wavelets", www.cs.wpi.edu/~matt/courses/cs563/talks/Wavelet_Presentation/, (Mar. 25, 1997), 1-6.

(Continued)

*Primary Examiner*—Krisna Lim
(74) *Attorney, Agent, or Firm*—Schwegman, Lundberg, Woessner & Kluth, P.A.

(57) ABSTRACT

An image data manipulation system is described in which users located remotely from an image data storage library may participate in a collaborative image data rendering and evaluation session. The system includes the exchange of state parameters between the client computer of a user controlling the image rendering, the session driver, and a server computer which relays updated state parameters to other client computers participating in a session. The state parameters are used to update the view on each users computer to keep all the displays of the participants in synch with that of the session driver. The server processes extensive image rendering task for which the remote clients are not equipped and transmits newly-processed image data to the clients as appropriate. One embodiment for educational applications utilizes pre-stored image data sets which eliminates the need to transmit large blocks of image data over a network during a collaborative session.

17 Claims, 5 Drawing Sheets

U.S. PATENT DOCUMENTS

| | | | |
|---|---|---|---|
| 5,432,871 A | 7/1995 | Novik | |
| 5,441,047 A | 8/1995 | David et al. | |
| 5,442,733 A | 8/1995 | Kaufman et al. | |
| 5,448,686 A * | 9/1995 | Borrel et al. | 345/420 |
| 5,469,353 A | 11/1995 | Pinsky et al. | |
| 5,482,043 A | 1/1996 | Zulauf | |
| 5,490,221 A | 2/1996 | Ransord et al. | |
| 5,497,435 A | 3/1996 | Beger | |
| 5,513,101 A | 4/1996 | Pinsky et al. | |
| 5,517,021 A | 5/1996 | Kaufman et al. | |
| 5,544,283 A | 8/1996 | Kaufman et al. | |
| 5,590,271 A | 12/1996 | Klinker | |
| 5,594,842 A | 1/1997 | Kaufman et al. | |
| 5,594,935 A | 1/1997 | Reber et al. | |
| 5,596,994 A | 1/1997 | Bro | |
| 5,603,323 A | 2/1997 | Pflugrath et al. | |
| 5,644,645 A | 7/1997 | Osuga | |
| 5,649,173 A | 7/1997 | Lentz | |
| 5,655,084 A | 8/1997 | Pinsky et al. | |
| 5,660,176 A | 8/1997 | Iliff | |
| 5,682,328 A | 10/1997 | Roeber et al. | |
| 5,715,823 A | 2/1998 | Wood et al. | |
| 5,730,146 A | 3/1998 | Itil et al. | |
| 5,740,267 A | 4/1998 | Echerer et al. | |
| 5,755,577 A | 5/1998 | Gilio | |
| 5,760,781 A | 6/1998 | Kaufman et al. | |
| 5,791,908 A | 8/1998 | Gillio | |
| 5,805,118 A | 9/1998 | Mishra et al. | |
| 5,836,877 A | 11/1998 | Zavislan | |
| 5,838,906 A | 11/1998 | Doyle et al. | |
| 5,847,711 A | 12/1998 | Kaufman et al. | |
| 5,882,206 A | 3/1999 | Gillio | |
| 5,883,976 A | 3/1999 | Ohsawa | |
| 5,903,775 A | 5/1999 | Murray | |
| 5,917,929 A | 6/1999 | Marshall et al. | |
| 5,941,945 A | 8/1999 | Aditham et al. | |
| 5,971,767 A | 10/1999 | Kaufman et al. | |
| 5,974,446 A | 10/1999 | Sonnenreich et al. | |
| 5,986,662 A | 11/1999 | Argiro et al. | |
| 5,987,345 A | 11/1999 | Engelmann et al. | |
| 6,008,813 A | 12/1999 | Lauer et al. | |
| 6,070,195 A | 5/2000 | Yamamoto | |
| 6,088,702 A | 7/2000 | Plantz et al. | |
| 6,105,055 A | 8/2000 | Pizano et al. | |
| 6,166,732 A | 12/2000 | Mitchell et al. | |
| 6,195,340 B1 | 2/2001 | Hatayama | |
| 6,211,884 B1 | 4/2001 | Knittel et al. | |
| 6,219,061 B1 | 4/2001 | Lauer et al. | |
| 6,222,551 B1 * | 4/2001 | Schneider et al. | 345/419 |
| 6,230,162 B1 | 5/2001 | Kumar et al. | |
| 6,243,098 B1 | 6/2001 | Lauer et al. | |
| 6,253,228 B1 * | 6/2001 | Ferris et al. | 709/203 |
| 6,260,021 B1 | 7/2001 | Wong et al. | |
| 6,262,740 B1 | 7/2001 | Lauer et al. | |
| 6,266,733 B1 | 7/2001 | Knittel et al. | |
| 6,760,755 B1 | 7/2001 | Brackett | |
| 6,272,470 B1 | 8/2001 | Teshima | |
| 6,283,322 B1 | 9/2001 | Liff et al. | |
| 6,283,761 B1 | 9/2001 | Joao | |
| 6,289,115 B1 | 9/2001 | Takeo | |
| 6,293,842 B1 | 9/2001 | Belt | |
| 6,297,799 B1 | 10/2001 | Knittel et al. | |
| 6,310,620 B1 | 10/2001 | Lauer et al. | |
| 6,313,841 B1 | 11/2001 | Ogata et al. | |
| 6,331,116 B1 | 12/2001 | Kaufman et al. | |
| 6,342,885 B1 | 1/2002 | Knittel et al. | |
| 6,343,936 B1 | 2/2002 | Kaufman et al. | |
| 6,344,861 B1 | 2/2002 | Naughton et al. | |
| 6,356,265 B1 | 3/2002 | Knittel et al. | |
| 6,362,620 B1 | 3/2002 | Debbins et al. | |
| 6,369,812 B1 | 4/2002 | Iyriboz et al. | |
| 6,369,816 B1 | 4/2002 | Knittel et al. | |
| 6,381,029 B1 | 4/2002 | Tipirneni | |
| 6,404,429 B1 | 6/2002 | Knittel | |
| 6,407,737 B1 | 6/2002 | Zhao et al. | |
| 6,407,743 B1 * | 6/2002 | Jones | 345/582 |
| 6,411,296 B1 | 6/2002 | Knittel et al. | |
| 6,421,057 B1 | 7/2002 | Lauer et al. | |
| 6,424,346 B1 | 7/2002 | Correll et al. | |
| 6,426,749 B1 | 7/2002 | Knittel et al. | |
| 6,430,625 B1 * | 8/2002 | Kley et al. | 709/246 |
| 6,476,810 B1 | 11/2002 | Simha et al. | |
| 6,483,507 B1 | 11/2002 | Osborne et al. | |
| 6,512,517 B1 | 1/2003 | Knittel et al. | |
| 6,514,082 B1 | 2/2003 | Kaufman et al. | |
| 6,532,017 B1 | 3/2003 | Knittel et al. | |
| 6,614,447 B1 | 9/2003 | Bhatia et al. | |
| 6,615,264 B1 * | 9/2003 | Stoltz et al. | 709/227 |
| 6,618,751 B1 * | 9/2003 | Challenger et al. | 709/213 |
| 6,621,918 B1 * | 9/2003 | Hu et al. | 382/128 |
| 6,654,012 B1 | 11/2003 | Lauer et al. | |
| 6,654,785 B1 * | 11/2003 | Craig | 709/203 |
| 6,674,430 B1 | 1/2004 | Kaufman et al. | |
| 6,680,735 B1 | 1/2004 | Seiler et al. | |
| 6,683,933 B1 | 1/2004 | Saito et al. | |
| 6,704,024 B1 | 3/2004 | Robotham et al. | |
| 6,807,558 B1 * | 10/2004 | Hassett et al. | 709/203 |
| 6,826,297 B1 | 11/2004 | Saito et al. | |
| 6,826,669 B1 | 11/2004 | Le et al. | |
| 6,847,365 B1 | 1/2005 | Miller et al. | |
| 6,847,462 B1 | 1/2005 | Kacyra et al. | |
| 6,879,996 B1 * | 4/2005 | Laves | 709/206 |
| 6,952,741 B1 * | 10/2005 | Bartlett et al. | 709/245 |
| 2001/0013128 A1 | 8/2001 | Hagai et al. | |
| 2001/0037402 A1 | 11/2001 | Schneider | |
| 2002/0005850 A1 | 1/2002 | Osborne et al. | |
| 2002/0065939 A1 * | 5/2002 | Liu | 709/248 |
| 2002/0069400 A1 | 6/2002 | Miloushev et al. | |
| 2003/0086595 A1 | 5/2003 | Hu et al. | |
| 2003/0156745 A1 | 8/2003 | Saito et al. | |

FOREIGN PATENT DOCUMENTS

| | | |
|---|---|---|
| EP | 1001369 A2 | 5/2000 |
| EP | 1001375 A2 | 5/2000 |
| EP | 1001377 A2 | 5/2000 |
| EP | 1001379 A2 | 5/2000 |
| EP | 1001380 A2 | 5/2000 |
| EP | 1054347 A2 | 11/2000 |
| EP | 1054348 A2 | 11/2000 |
| EP | 1054349 A2 | 11/2000 |
| EP | 1054351 A2 | 11/2000 |
| EP | 1054355 A2 | 11/2000 |
| EP | 1054356 A2 | 11/2000 |
| EP | 1054357 A2 | 11/2000 |
| EP | 1054358 A2 | 11/2000 |
| EP | 1054359 A2 | 11/2000 |
| EP | 1054383 A2 | 11/2000 |
| EP | 1054384 A2 | 11/2000 |
| EP | 1054385 A2 | 11/2000 |
| EP | 1069528 A2 | 1/2001 |
| EP | 1069530 A2 | 1/2001 |
| EP | 1069532 A2 | 1/2001 |
| EP | 1071041 A2 | 1/2001 |
| EP | 1081651 A2 | 3/2001 |
| EP | 1081652 A2 | 3/2001 |
| EP | 1081653 A2 | 3/2001 |
| EP | 1089225 A2 | 4/2001 |
| EP | 1089234 A2 | 4/2001 |
| EP | 1089235 A2 | 4/2001 |
| EP | 1093085 A2 | 4/2001 |
| EP | 1195717 A2 | 4/2002 |
| EP | 1195718 A2 | 4/2002 |
| EP | 1195719 A2 | 4/2002 |

| | | |
|---|---|---|
| EP | 1195720 A2 | 4/2002 |
| EP | 1209618 A1 | 5/2002 |
| EP | 1209629 A1 | 5/2002 |
| JP | 11-239165 | 8/1999 |
| JP | 2002-183746 | 6/2002 |
| JP | 2002-183747 | 6/2002 |

OTHER PUBLICATIONS

"Brief Description of the Gibabit Testbed Initiative", http://www0.cnri.reston.va.us/overview/html,(observed Jul. 15, 1999), 7 pp.

"A Prototype Distributed Visualization System", http://www.hpcc.arc.nasa.gov/reports/annrep97/ess/ww42.htm, (observed Oct. 5, 1999), 11 pp.

"Adding Data Visualization to Instrumentation", (Advanced Visual Systems, Inc.) http://www.avs.com/solution/success/papers/testmea.htm,(observed Jul.15, 1999),6 pp.

"An Interactive Remote Visualization Environment for an Electromagnetic Scattering Simulation on A High Performance Computing System", http://www.npac.syr.edu/users/gcheng/CEM/ems.html,(observed Jul. 14, 1999), 2 pp.

"Argonne-USC Researchers Win GII Next Generation Award for Advanced Computing Infrastructure", http://www.npaci.edu/News/98/042298-gusto.html,(observed Jul. 15, 1999),2 pp.

"Corridor One: An Integrated Distance Visualization Environment for SSI and ASCI Applications", (Proposal to DOE 99-09) http://www-fp.mcs.anl.gov/fl/research/Proposals/co.htm,(observed Oct. 5, 1999),29 pp.

"Demand for General Availability of Visualization Techniques", http://www.ts.go.dlr.de/sm-sk_info/library/documents/EGSciVis97/VaWX5Fproto-3.html,(observed Jul. 15, 1999),1 p.

"Department of Defense High-Performance Computing Modernizatiion Office", http:/www.ncsa.uiuc.edu/Vis/PET/, (observed Jul. 15, 1999), 1 p.

"Distributed Visualization Task - 1995 HPCC Annual Review Reports", http://olympic.jpl.nasa.gov/Reports/Highlights95/ML_DVT.html,(observed Jul. 15, 1999), 1 p.

"DOD PET - Trends in Graphics and Visualization", http://www.ncsa.uiuc.edu/Vis/Publications/trends.html,(Jan., 1998), 3 pp.

"DOD PET Strategic Plan for Visualization", http://www.ncsa.uiuc.edu/Vis/PET/strategy.html,(observed Jul. 15, 1999), 1 p.

"DOD PET Visualization Plan, PET Initiatiives", http://www.ncsa.uiuc.edu/Vis/PET/timelineEfforts.html,(observed Jul. 15, 1999), 1 p.

"DOD PET Visualization Plan, Technology Trends", http://www.ncsa.uiuc.edu/Vis/PET/timelineTrends.html, (observed Jul. 15, 1999), 1 p.

"DOD Pet Visualization Plan, User Needs", http://www.ncsa.uiuc.edu/Vis/PET/timelineNeeds.html,(observed Jul. 15, 1999), 1 p.

"EMERGE - Application Projects/Toolkits that will be deployed over EMERGE", http://www.evl.uic.edu/cavern/EMERGE/applications.html,(observed Oct. 7, 1999),2 pp.

"ERSUG Meeting Minutes", http://home.nersc.gov/about/ERSUG/meeting_info/Apr98_minutes.html,(observed Jul. 15, 1999),6 pp.

"Experiments in Remote Visualization", http://woodall.ncsa.uiuc.edu/dbock/projects/RemoteViewIndex.html, (observed Jul. 14, 1999),2 pp.

"Gibabit Testbeds Final Report", http://www.cnri.reston.va.us/gigafr/noframes/section-4-25.htm,(observed Jul 14, 1999), 4 pp.

"H Innovation Trade Show Brochure", (2001),2 pp.

"High Performance Internet Access for Research and Education in Science and Engineering", (The State University of New Jersey - Rutgers - Grant Proposal) http://ephesus.rutgers.edu/hypernet/origprop.net,(observed Jul. 15, 1999), 10 pp.

"HP Internet Philanthropic Initiative - 1998 Update", http://www.informed.dia.fi.upm.es/english/HP/proposal1998.html,(observed Oct. 5, 1999),8 pp.

"Internet 2 Research Applications", (University of Alabama at Birmingham) http://www.uab.edu/internet2/meritapps1.html,(observed Jul. 15, 1999). 1 p.

"Introduction - Data Visualization", http://www.npac.syr.edu/users/gcheng/homepage/thesis/node27.html.(observed Jul. 15, 1999),2 pp.

"NCSA Report, SIGGRAPH 98: Visualization Software", http://www.ncsa.uiuc.edu/Vis/Publications/SIGGRAPH98/s10.html,(observed Jul. 15, 1999),1 p.

"NCSA Vis&VE Trip Report: IEEE VR 99 (nee VRAIS99)", http://www.ncsa.uiuc.edu/Vis/Trips/VR99.html,(observed Jul. 15, 1999),12 pp.

"NCSA Visualization and Virtual Environments", http://www.ncsa.uiuc.edu/Vis/,(observed Jul 15, 1999),2 pp.

"Next Generation Internet - 1999 Program", http://www.er.doe.gov/production/octr/mies/press99-09.html, observed Oct. 12, 1999),2 pp.

"Northeast Parallel Architectures Center - Projects", http://www.npac.sry.edu/Projects.index.html,(observed Jul. 15, 1999), 4 pp.

"Northeast Parallel Architectures Center - Mission", http://www.npac.syr.edu/Mission/index.html,(observed Oct. 12, 1999),1 p.

"Notice Inviting Research Grant Applicaitons", *Federal Register, vol. 64, No. 5*, (Jan. 8, 1999),3 pp.

"PACS - Picture Archiving and Communications Systems", http://www.medfusion.com/Arena/PACS/pacs.html, (observed Oct. 12, 1999),1 p.

"Progressive Image Transmission", www.vision.ee.ethz.ch/~rsia/talks/RSL_talk/pit 3.html. 1 p.

"Rationale for A WWW-Based Visualization Service", http://www.ts.go.dlr.de/sm-sk_info/library/documents/EGSciVis97/VaWX5Fproto-2.html,(observed Jul. 15, 1999),1 p.

"Scientific Visualization Sites (Mirror)", http://puh.cb.uu.se/~rogerh/visWeblets.html,(observed Oct. 5, 1999),5 pp.

"TeraRecon's AquariusNET™ Server", (2002), 7 pp.

"The Clinical Practice Guidelines Project", http://www.infomed.dia.fi.upm.es/english/guidelines.html,(observed Oct. 7, 1999),2 pp.

"The Realization Report: Issue No. 3", http://www.itd.nrl.navy.mil/ONR/realization_report/ rosenblum.003.html, (observed Jul. 15, 1999),4 pp.

"Use of Remote Visualization Methods", http://www.ts.go.dlr.de/sm-sk_info/library/documents/EGSciVis97/VaWX5Fproto-4.html,(observed Jul. 15, 1999), 1 p.

"Vol. III - Technical Proposal for Collaborative Interaction and Visualization", (BAA 93-01-PKRD) http://www.npac.syr.edu/users/gcf/romelabciv/prop.html,(observed Oct. 12, 1999),28 pp.

"Web-Based Visualization Server for 3D Reconstruction", http://felix.uttgm.ro/~dradoiu/ip/Laborator/application.html,(observed Oct. 12, 1999), 4 pp.

ANG, C. S., et al., "Integrated Control of Distributed-Volume Visualization Through the World-Wide-Web",

*Proceedings of the IEEE Conference Visualization '94*, (1994), 13-20.

BAJAJ, C. L., et al., "The VAIDAK Medical Image Model Reconstruction Toolkit", *Proceedings of the 8th SIGAPP Symposium on Applied Computing*, (Abstract Only),(1993), 1 p.

Baker, M. P., et al., "Battleview: Touring a Virtual Battlefield", http://www.ncsa.uiuc.edu/Vis/Publications/bv98.html,(observed Jul. 15, 19999),5 pp.

Baker, M. P., et al., "Visualization of Damaged Structures", http://www.ncsa.uiuc.edu/Vis/Publications/damage.html, (observed Jul. 15, 1999),6, pp.

Bock, D., et al., "Collaborative Visualization", http://www.ncsa.uiuc.edu/Vis/Publications/collabFramework.html, (observed Jul. 15, 1999),6 pp.

Bock, D., "Remote Visualization Using the World Wide Web", http:www.ncsa.uiuc.edu/Vis/Publications/remote/VisHTTP.html,(observed Jul. 15, 1999),5 pp.

Bossart, P.-L., "Hypertools in Image and Volume Visualization", *Proceedings of the Fourth Annual Tcl.Tk Workshop*, (Abstact Only),(1996),1 p.

Casey, B., "HInnovatin Adds Internet Wrinkle to 3-D Imaging", http://www.auntminnie.com/index.asp?sec=rca&sub=def&pag=dis&ItemID=50700,(observed Dec. 11, 2002),1 p.

Cavanagh, P. M., et al., "Commentary - Delivering Imaging to Primary Care in the Next Millennium", *The British Journal of Radiology, 71*, (1998),805-807.

Chen, L. S., et al., "A Distributed and Interactive Three-Dimensional Medical Image System", *Computerized Medical Imaging and Graphics, 18(5)*, (1994),325-337.

Cimino, C., et al., "Clinical Applications of an ATM/Ethernet Network in Departments of Neuroradiology and Radiotherapy", *Stud Health Technol Inform., 43(Part B)*, (1997),606-610.

Coleman, J., et al., "TeleInViVo: A Collaborative Volume Visualization Application", *Stud Health Technol Inform. 39*, (1997),115-124.

Cosic, D., "An Open Medical Imaging Workstation Architecture for Platform-Independent 3-D Medical Image Processing and Visualization", *IEEE Transactions on Information Technology in Biomedicine, 1(4)*, (1997),279-83.

Dobbins, H., et al., "Multisite Three-Dimensional Brain Visualization", http://www.uab.edu/internet2/ala_tele-collaboration.html,(observed Oct. 12, 1999),1 p.

Eichelberg, M., et al., "RETAIN: Multimedia Teleradiology on the Pan-European Information Superhighway", *CAR' 96 Computer Assisted Radiology. Proceedings of the International Symposium on Computer and Communication Systems for Image Guide Diagnosis and Therapy*, (Abstract Only),(1996),1 p.

Fernandez, I., et al., "ARMEDA: Accessing Remote Medical Databases Over the World Wide Wide", http://www.infomed.dia.fi.upm.es/Armeda/armeda_MIE97.html, (observed Oct. 7, 1999),4 pp.

Furuie, S., et al., "Telemedicine: Remote Analysis and Quantification of Nuclear Medicine Images Using Java", http://incor.usp.br/spdweb/projects/p22/p22.html,(observed Oct. 12, 1999),2 pp.

Hendin, O., et al., "Medical Volume Rendering Over the WWW Using VRMP and JAVA", *Stud Health Technol Inform.. 50*, (1998),34-40.

Henri, C. J., et al., "Design and implementation of World Wide Web-based tools for image management in computed tomography, magnetic resonance imaging, and ultrasonography", *Journal of Digital Imaging, 10(3 Suppl 1)*, (1997),77-79.

Hightower, D., et al., "Computer Radiology: Ship to Shore", *CAR '96 Computer Assisted Radiology. Proceeding of the International Symposium on Computer and Communication Systems for Image Guided Diagnosis and Therapy*, (Abstract Only),(1996),1 p.

Kim, N., et al., "Web Based 3-D Medical Image Visualization on the PC", *Proceedings of the 9th World Congress on Medical Informatics MEDINFO '98, 9 (Part 2)*, (1998), 1105-1110.

Kindratenko, V., et al., "Sharing Virtual Environments Over a Transatlantic ATM Network in Support of Distant Collaboration in Vehicle Design", http://www.ncsa.uiuc.edu/VEG/DVR/VE98/article.html,(observed Jul. 15, 1999),8 pp.

Lee, J. S., et al., "Volumetric Visualization of Head and Neck CT Datas for Treatment Planning", *International Journal of Radiology, Oncology, Biology, Physics, 44(3)*, (Abstract Only),(1999),2 pp.

Leigh, J., et al., "LIMBO/VTK: A Tool for Rapid Tele-Immersive Visualization", *Proceedings of IEEE Visualization '98*, (1998)4 pp.

Liu, P.-W., et al., "Distributed Computing: New Power for Scientific Visualization", *IEEE Computer Graphics and Applications, 16 30*, (1996),42-51.

Lu, T., et al., "Compression Techniques in Teleradiology", *Proceedings of the SPIE (vol. 3808), Applications of Digital Image Processing XXII*, (Abstract Only),(1999),1 p.

Macedonia, M. R., et al., "A Transatlantic Research and Development Environment", *IEEE Computer Graphics and Applications, 17(2)*, (1997), 76-82.

Makris, L., et al., "Teleworks: A CSCW Application for Remote Medical Diagnosis Support and Teleconsultation", *IEEE Transactions on Information Technology in Biomedicine, 2(2)*, (Jun. 1998),62-73.

Malassiotis, S., et al., "Coding and Visualization oof 3D Medical Data for Low Bitrate Communication", *CAR '96 Computer Assisted Radiology. Proceedings of the International Symposium on Computer and Communication Systems for Image Guided Diagnosis and Therapy*, (Abstract Only),(1996),1 p.

Markle, S., et al.,"Distributed Visualization - How to imporve the Quality of 3D medical volume rendering at almost no costs", Europacs, Oct. 1998.

Martin, D. C., et al., "Libraries in the Information Age", http://www.ckm.ucsf.edu/papers/LibraryInformationAge/, (observed Oct. 5, 1999),3 pp.

Mercurio, P. J., et al., "The Distributed Laboratory: An Interactive Visualization Environment of Electron Microscope and 3D Imaging", http://www.acm.org/pubs/toc/Abstracts/cacm/129891.html,(observed Jul. 15, 1999),2 pp.

Mun, S. K., et al., "Health Care Using High-Bandwidth Communicaiton to Overcome Distance and Time Barriers for the Department of Defense", *Proceedings of the SPIE (vol. 1785) - Enabling Technologies for High-Bandwidth Applications*, (Abstract Only),(1993),1 p.

Napel, S., "3D Displays for Computed Tomography", *In: Medical CT and Ultrasound: Current Technology and Applications*, Published by Advanced Medical Publishing, (1995),603-626.

Norris, P. R., et al., "Reliable Remote Visualization of Real-Time Biomedical Data", (Abstract Only),(1998),1 p.

Orphanoudakis, S. C., et al., "Technological advance in Teleradiology", *European Journal of Radiology, 22(3)*, (Jun. 1996),205-217.

Pandya, A. S., et al., "3D Reconstruction, Visualization, and Measurement of MRI Images", *Proceedings of the SPIE (vol. 3640) - Three-Dimensional Image Capture and Applications II*, (Abstract Only),(1999),1 p.

Pelizzari, S. A., et al., "Volumetric Visualization of Anatomy for Treatment Planning", *International Journal of Radiation, Oncology, Biology, Physics, 34(1)*, (Abstract Only), (1996),2 pp.

Phalke, V., "Remote Visualization for Computational Simulations", http://www.science.doe.gov/sbir/awards_abstracts/sbir/cycle16/phase1/024.htm,(observed Oct. 12, 1999),1 p.

Prior, F., et al., "Communication Technology for Telemedicine", *Proceedings of the National Forum: Military Telemedicine On-line Today Research Practice and Opportunities*, (1995),1 p.

Rhee, T. H., et al., "An Effective Visualization Technique for Huge Volume Data", *Journal of KISS(A) (Computer Systems and Theory)*, (Abstract Only),(1997),1 p.

Robb, R. A., et al., "Patient-Specific Anatomic Models from Three Dimensional of Medical Image Data for Clinical Applications in Surgery and Endoscopy", *Journal of Digital Imaging, 10(3,1)*, (Abstract Only),(1997),1 p.

Roush, W., "To Johnson, the Grid Means Access", *NAS News*, (1999),2 pp.

Ruggiero, C., "Teleradiology: A Review", *Journal of Telemedicine and Telecare, 4*, (1998), 25-35.

Sakamoto, Y., et al., "Three-Dimensional Segmentation of Magnetic Resonance Images Using Neural Network", *Proceedings of ACCV '95. Second Asian Conference on Computer Vision, vol. 1*, (Abstract Only),(1995), 1 p.

Salomie, A., et al., "A Teleworking Tool With Progressive Transmission Capabilities for Medical Images", *CARS '99 Computer Assisted Radiology and Surgery, Proceedings of the 13th International Congress and Exhibition*, (Abstract Only),(1999), 1 p.

Samothrakis, S., et al., "WWW Creates New Interactive 3D Graphics and Collaborative Environments for Medical Research and Education", *International Journal of Medical Informatics, 47(1-2)*, (1997),69-73.

Santarelli, M. F., et al., "A Parallel System for Dynamic 3D Medical Imaging", *Proceedings of High-Performance Computing and Networking. International Conference and Exhibition*, (Abstract Only),(1997),1 p.

Silverstein, et al., "Web-Based Segmentation and Display of Three-Dimensional Radiologic Image Data", *Stud Health Technol Inform., 50*, (1998),53-59.

Smith, P. H., et al.,"Data and Visualization Corridors: Report on the 1998 DVC Workshop Series", Rosedale, California Institute of Technology Report CACR-164,(Sep., 1998),54 pp.

Wilkinson, E. P., et al., "Remote-Rendered 3D CT Angiography (3DCTA) as an Intraoperative Aid in Cerebrovascular Neurosurgery", *Computer Aided Surgery, 4*, (1999),256-263.

Wong, S. T., et al., "Interactive Query and Visualization of Medical Images on the World Wide Web", http://web.archive.org/20000412115341/http://www.lri.ucsf.edu/polymap/paper/spie96.html (Archived Apr. 12, 2000), 11 pp.

Yun, D. Y., et al., "Sharing Computational Resources and Medical Images Via ACTS-Linked Networks", PTR Jun. 1996, http://web.ptc.org/library/ptr/june96/2.html, observed Nov. 3, 2003, 14 pp.

Zuiderveld, K. J., et al., "Clinical Evaluation of Interactive Volume Visualization", *Proceedings of the 7th Conference on Visualization '96*, (1996),367-370.

* cited by examiner

| State Parameter | Description |
|---|---|
| 1 communication parameters | |
| int dataLen; | length of data (in byte) to be transmitted |
| int Compressed; | non zero if the data is compressed |
| .... | |
| 2 data and display parameters | |
| int rowSize, columnSize; | The x and y dimension of the image being transmitted |
| int ImageRenderingMethodUsed; | 0:Multislice; 1:Axial; 2:Sagittal; 3:Coronal; 4:Oblique; 5:Volume Render; 6:MIP; 7:Average; 8: MinIP; 9: Double Oblique; |
| int wwwl[2] | Window width and level for the image to be displayed |
| int pan_center[2] | The center of display field of view in the original dataset coordinate system: 0 nmax-1 for x,y. The default is the center of the full image. |
| int zoom_factor | The image's zoom-factor |
| float spacing | The pixel spacing |
| float rotationMatrix4x4[4][4] | Rotation matrix for current rendering. |
| int croppingBoundary3D[6] | Field of View, given in dataset coordinate system: xmin, xmax, ymin, ymax, zmin, zmax. |
| float center_ob_plane[3] | The center of oblique plane |
| float oblique_thickness | The thickness of the oblique plane |
| .... | |
| 3. collaboration parameters | |
| int conference_flag | Conference flag |
| int driver_ID | Driver's ID |
| structured annotation | Recording the cursor position and any annotation and text on the driver's computer. |
| Participant list | The list of designated participants |
| .... | |

ON-LINE IMAGE PROCESSING AND COMMUNICATION SYSTEM

BACKGROUND OF THE INVENTION

The present invention generally relates to miniPACS (Picture Archiving and Communications System) or teleradiology systems, specifically to miniPACS/teleradiology systems with remote volume data processing, visualization, and multi-user conferencing capability. In our previous patent application, U.S. patent application Ser. No. 09/434,088, now U.S. Pat. No. 6,621,918 issued Sep. 16, 2003 we presented a miniPACS/teleradiology system with remote volume data rendering and visualization capability. The present invention is directed to additional features and enhancements of the architecture described therein.

Teleradiology is a means for electronically transmitting radiographic patient images and consultative text from one location to another. Teleradiology systems have been widely used by healthcare providers to expand the geographic and/or time coverage of their service and to efficiently utilize the time of healthcare professionals with specialty and subspecialty training and skills (e.g., radiologists). The result is improved healthcare service quality, decreased delivery time, and reduced costs.

One drawback to some existing teleradiology systems, however, is the lack of the ability for radiologists to communicate interactively with their colleagues and referring physicians from disparate locations for the purpose of consultation, education, and collaborative studies. Collaboration is especially important for studies using volumetric images, where the ability to interactively manipulate the volumetric images and simultaneously view the processed images is essential for rapid and effective communications between multiple participants involved.

There are numerous methods and systems providing multi-media network based conferencing capability. However, these methods and systems only support shared viewing of texts, documents, and videos. Furthermore, a radiology conferencing system presents unique obstacles. For example, the size of data to be transmitted could be very large and the requirement on image (picture) quality could be very high. To be clinically useful, the transmission should be interactively "on-demand" in nature. There are on-going efforts to develop radiology conferencing capabilities for the communication of two-dimensional (2D) images. However, none of these systems supports interactive communication of volumetric/three-dimensional (3D) images.

As a result, there exists a need for a miniPACS/teleradiology system with network based conferencing capability supporting synchronized distribution and viewing of interactively processed volumetric images. Further, there exists a need for an improved method and procedure for the management of multi-center trials involving volumetric images.

SUMMARY OF THE INVENTION

The present invention provides a computer architecture for a client/server-based advanced image processing and rendering system. The present invention further provides a computer architecture to support multi-user concurrent usage of the processing server. The present invention includes a method and apparatus that combines the network-based conferencing capability with remote interactive advanced image processing capability. The present invention enables users from disparate locations to interactively manipulate images and simultaneously view the processed images in an independent or synchronized fashion. The present invention further enables a user to interactively view and manipulate the images without having to download the entire volumetric data set. The present invention also includes improved methods and procedures for radiology consultation and multi-center trial management involving volumetric images using the above-mentioned technology.

The present invention may be used for radiology consultation. In one step, the acquisition of 2D or 3D/volumetric image/data sets or retrieval of previously acquired image/data sets is performed. The volumetric data set could be three-dimensional in space, or two- or three-dimensional in space and one-dimensional in time, e.g., time-resolved spatial data sets. In another step, data is moved to a server, which could be the scanner workstation itself or a separate computer connected to a network, and which has the conferencing software. In another step, client software is initiated by a remote user/users. Each user is able to remotely access and manipulate the 2D as well as volumetric/3D images with full processing capabilities, including Multiplanar Reformat (MPR), Maximum Intensity Projection (MIP), Volume Rendering, Image segmentation, and etc. As described in the preferred embodiment, an user may send the image processing request, such as MPR request to the server, the server will render the images accordingly and send the result back. In another step, each user is able to interactively manipulate volumetric images without transferring the entire dataset, employing an "on-demand" image transmission method.

DETAILED DESCRIPTION OF THE PREFERRED EMBODIMENT

Figure 1:
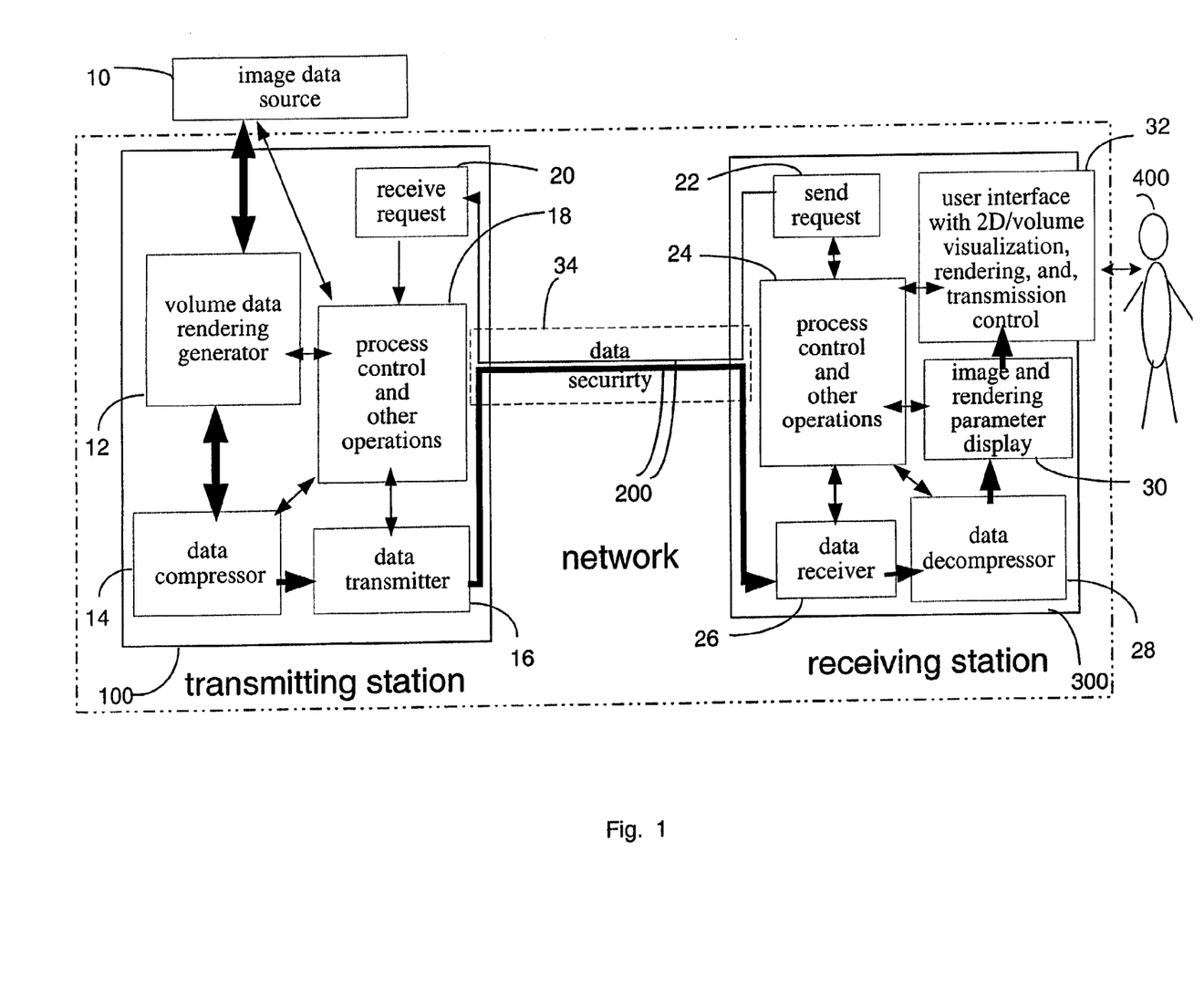
FIG. 1 depicts a block diagram of the present invention.

FIG. 1 depicts the teleradiology system described in our previous patent application, U.S. patent application Ser. No. 09/434,088. Now, U.S. Pat. No. 6,621,918 issued Sep. 16, 2003. The teleradiology system includes as data transmitting station 100, a receiving station 300, and a network 200 connecting the transmitting station 100 and receiving station 300. The system may also include a data security system 34 which extends into the transmitting station 100, receiving station 300, and network 200. Receiving station 300 comprises a data receiver 26, a send request 22, a user interface 32, a data decompressor 28, a display system 30, a central processing system 24, and, data security 34. Transmitting station 100 comprises a data transmitter 16, a receive request 20, a data compressor 14, a volume data rendering generator 12, a central processing system 18, and, data security 34.

Many image visualization and processing tasks (such as volume rendering) consist of multiple interactive sub-tasks. For example, visualizing a dataset consists of at least two steps (subtasks): 1) generating a processed image to be displayed; 2) displaying the image. In a client/server-based image processing system, some subtasks are performed by the client and the other by the server. Using the above example, generating the processed image to be displayed can be performed in entirety on the server, or, partially on the server and partially on the client. Displaying the processed image is performed on the client.

Figure 2:
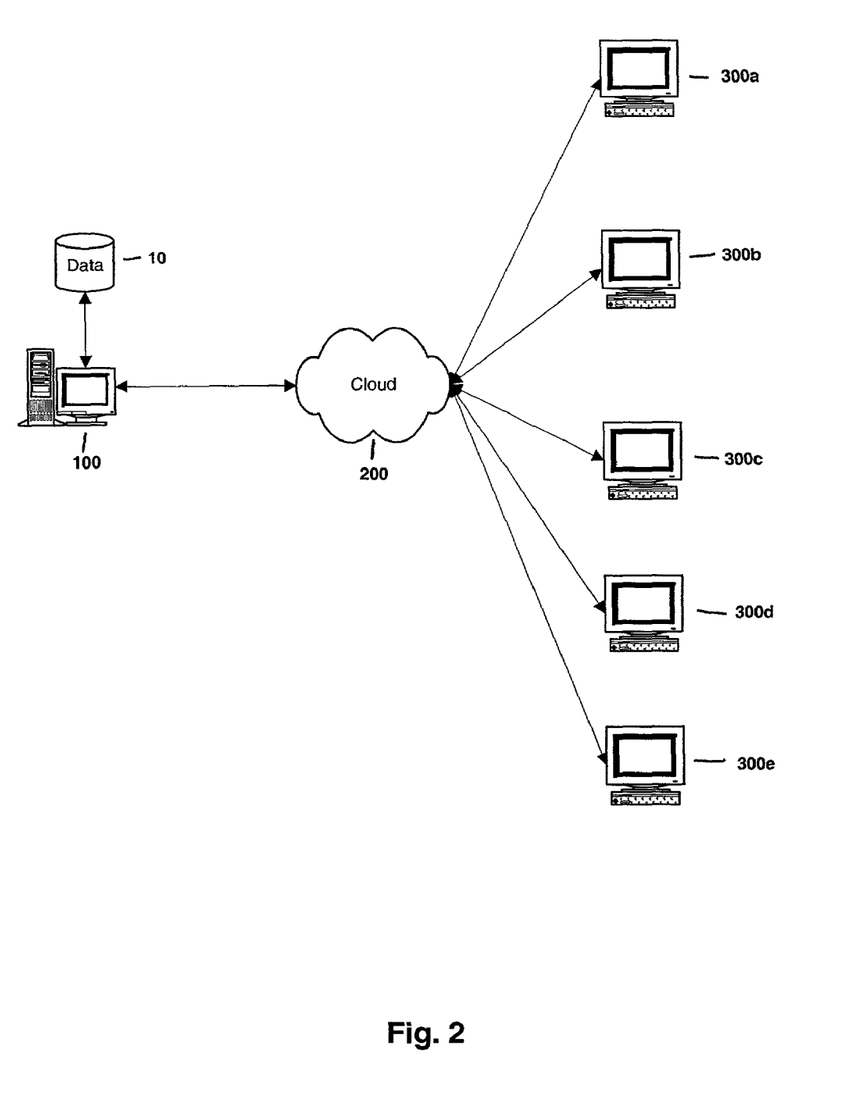
FIG. 2 depicts an alternative diagram of the present invention.

Referring now to FIG. 2, a system is shown wherein, as contemplated in the present invention, several receiving stations 300a–e have access over a network 200 to a transmitting station. Each of the receiving stations 300a–e are structured similarly to the receiving station 300 shown in FIG. 1. The transmitting station may be considered the server and the receiving stations the clients to use the client/server terminology.

Figure 3:
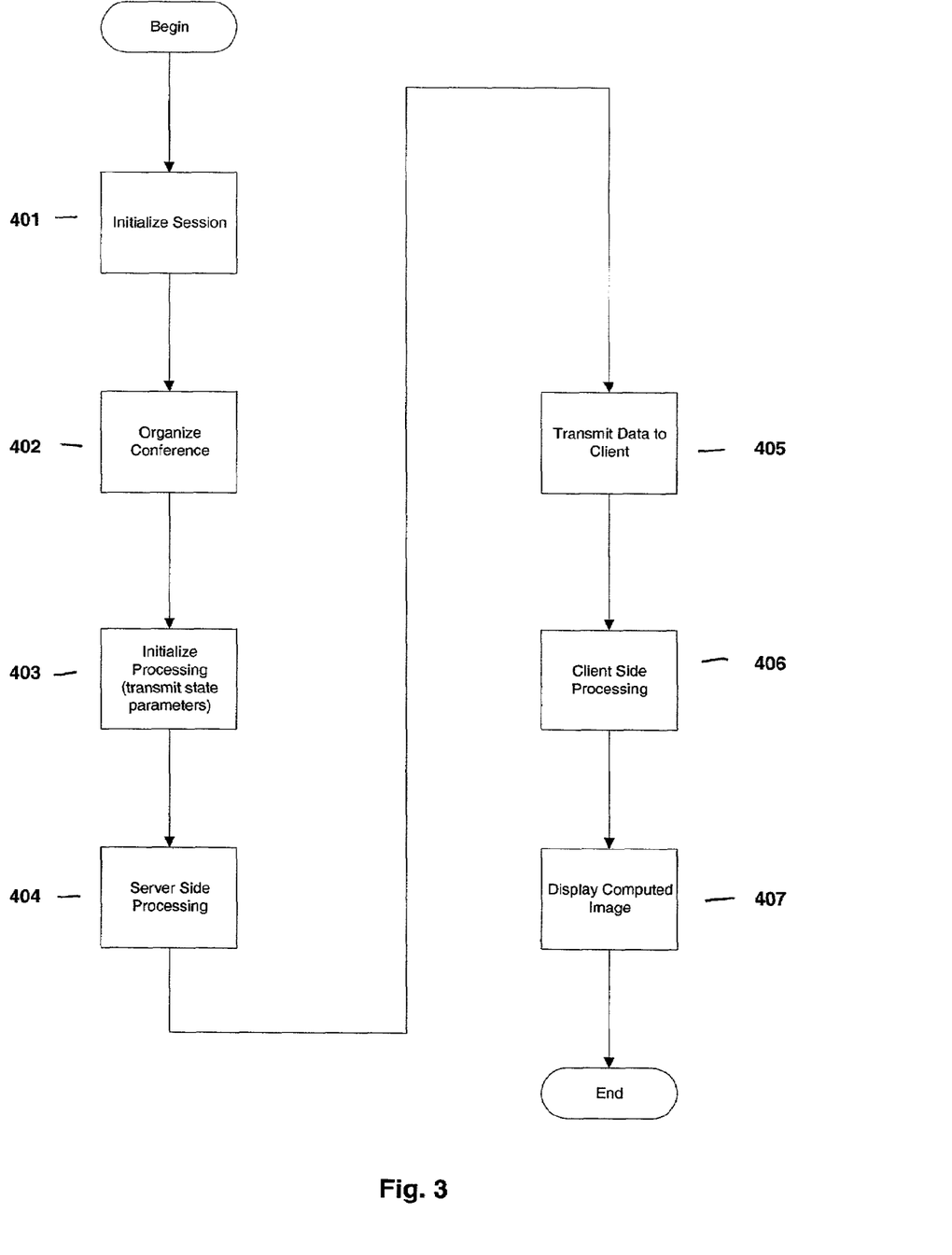
FIG. 3 depicts a flowchart of method of the present invention.

Referring now to FIG. 3, a flow chart representing steps performed according to one preferred embodiment is shown. At step 401, one or more users initiate a session by logging in to the server from one of the receiving stations 300a–e. At step 402, one of the logged in users issues a command to form a conference, and identifies a list of users who may participate in the conference. The user who initiates the conference, e.g., the user at receiving station 300a shown in FIG. 2, may be designated as the conference "driver" by default. The conference driver may be, for example, a consulting radiologist. Other designated conference participants may join the conference. Alternatively, the driver may review the list of users logged in and select persons to participate in the conference. The other participants may be, for example, 3D technologists, other radiologists, referring physicians, or other healthcare personnel. The driver has the ability to accept or reject a request to join. Alternatively, the driver may designate that the conference is "open," i.e., that other users may join in without an express authorization being made by the driver.

Figure 4:
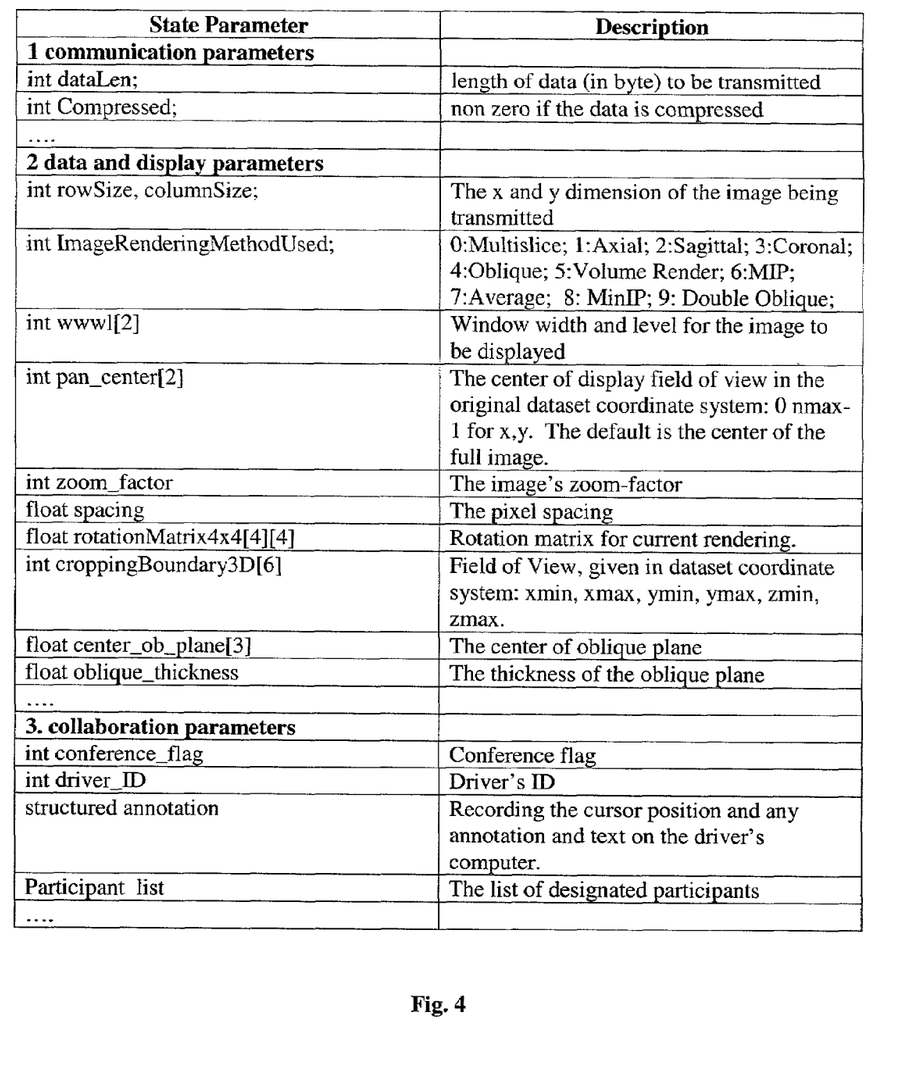
FIG. 4 depicts a description of state parameters which may be used in one embodiment.

At step 403, the driver initiates a processing command from the client side. In a preferred operation, the driver, using interface 32, specifies: 1) at least one image data set to be visualized; 2) at least one data rendering method to be used; 3) the rendering parameters used by each rendering method, 4) data compression parameters, and 5) the data transmission parameters for controlling data transmission over network 200. Examples of state parameters are provided in FIG. 4. In particular, the driver may, via user interface 32, adjust rendering parameters, e.g., viewpoint, spatial region, and value range of the data to be rendered, and other settings. The techniques for setting and adjusting these parameters include 1) using preset protocols for some typical settings; 2) inputting a specific setting with a keyboard, a mouse and/or other input devices; and/or 3) interactive navigation using a mouse, a trackball, a joystick, a keyboard and/or other navigating devices. This driver may, via user interface 32, edit (including process) patient data, e.g., remove the bone structures, in a manner similar to the current volume data rendering/visualization systems. With the teleradiology system of the invention, driver can, via user interface 32, define and adjust data rendering methods and parameters, control what is to be rendered, transmitted and visualized next, and eventually obtain the final rendering result. A central processing system 24 on the driver's receiving station receives and validates the driver's request. The central processing system 24 then issues the request, which is sent via send request 22 to transmitting station 100 through network 200.

At step 404, the central processing system 18 on the transmitting station 100 receives the request via receive request 20. Coordinated by central processing system 18, volume data rendering generator 12 accesses from image data source 10 the image data set which the user has specified, and then generates the data rendering result based on the data rendering method and parameters which the user has specified. The rendering result may be a 2D image, much smaller in size than the original data set.

At step 405, the data transmitter 16 on transmitting station 100 transmits the compressed data to data receiver 26 on receiving stations 300a–e which have sent a request for image data, i.e., on-demand, via network 200 based on data transmission parameters which the user has specified. The on-demand feature of the present invention will be describe further in connection with FIG. 5. For the teleradiology system of the invention, the preferred transmission medium (i.e., network 200) may be an intranet, the Internet (including the Internet2) or a direct dial-up using a telephone line with a modem. The preferred data transmission protocol is the standard TCP/IP, although the method may be adapted to accommodate other protocols. Furthermore, for some transmission media (e.g., the Internet2), user 400 can control certain aspects (e.g., the priority level, the speed) of data transmission by selecting transmission parameters via user interface 32.

At step 406, the central processing systems 24 of the various receiving stations 300a–e coordinate the client-side processing. If needed, data decompressor 28 decompresses (or restores) the rendering result. The central processing system 24 may also perform further image processing and operations. The processing is performed in which the final image is computed based on the field of view and the image window/level (i.e., brightness/contrast) settings currently prescribed by the conference driver.

At step 407, the display systems 30 at receiving stations 300a–e display the computed image and other parameters. Via user interface 32, the driver may further modify parameters, including 1) the image data set to be visualized, 2) the data rendering method to be used, 3) the rendering parameters used, and 4) the data transmission parameters used. This process goes on until a satisfactory rendering and visualization result is obtained.

The set of image processing and display parameters, collectively called state parameters, keep track of the effect of image processing, performed either at the server or at a client, and if needed, synchronize the display (viewing) of multiple users. Examples of state parameters are given in FIG. 4. Each time when a new subtask is performed, this set of the state parameters is updated at the server. Any further image processing and display task will be performed based on this set of updated state parameters.

In one embodiment, the resulting images are "pulled" to the clients from the server. When a client with the driver authorization prescribes an operation and regardless of whether this operation is performed on the client, the server, or the both, the state parameters will be updated on both the server and the driving client to reflect the resultant change due to this operation. Other clients periodically compare their local copy of the state parameters with the copy on the server. If some differences are found that require updating the local display, that client will issue the update request. Again, depending on the division of subtasks, some requests are fulfilled by the client only, while the others require that the server sends updated image/information.

Figure 5:
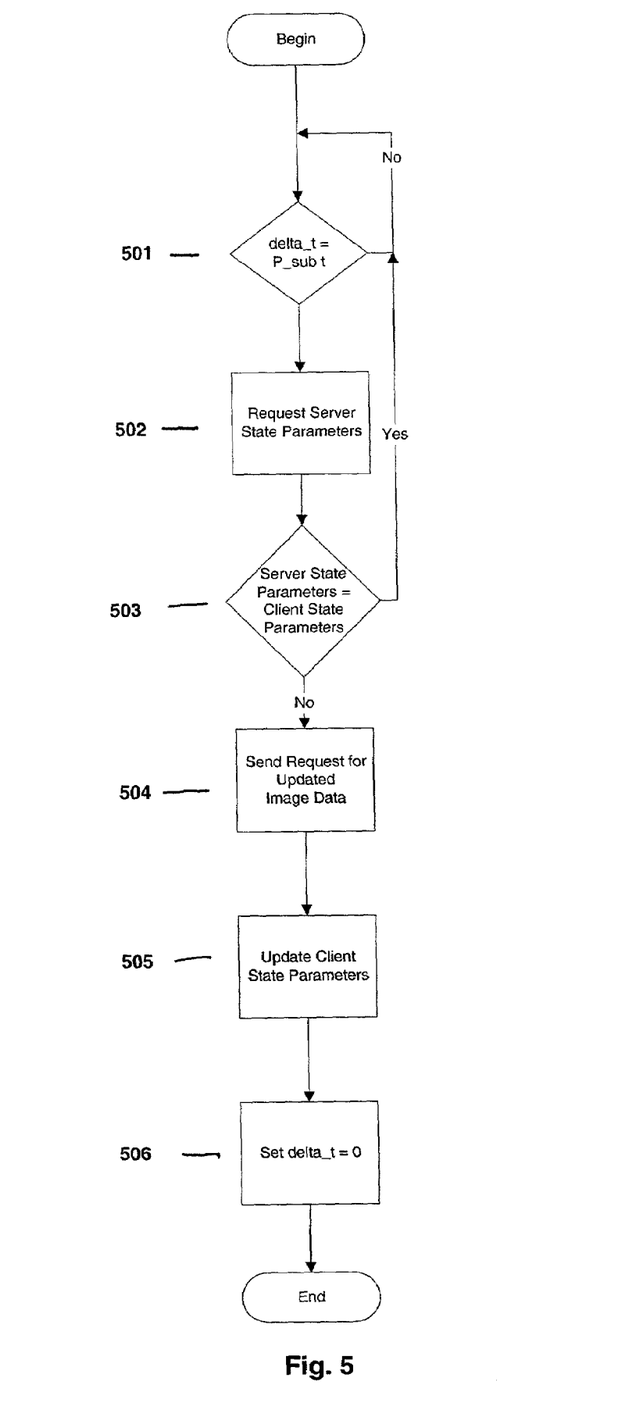
FIG. 5 depicts a flowchart of the state parameter updating method.

Referring now to FIG. 5, the steps involved in state parameter updating will be described. State parameter updating is controlled by the client-side conferencing software running on receiving stations 300a–e. At step 501, a check is made with a system clock, or another timing source, to determine whether the amount of time that has elapsed since the last state parameter update, $\Delta t$, is equal to a predetermined timing parameter, $P_t$, which determines the frequency with which the state parameters are updated. If $\Delta t \leq P_t$, then step 502 is performed. If $\Delta t < P_t$, then control returns to the beginning of the routine. For example, $P_t$ may be 0.25 to 0.5 seconds. At step 502, one of the receiving station 300 sends a request to the transmitting station for current state parameters associated with the current conferencing session. At step 503, the receiving station 300 compares the state parameters which have been stored locally to the state parameters that are received from the transmitting station after the request made in step 502. If the client state parameters and the server state parameters are equal, then control returns to the beginning of the routine. If the two sets of parameters are not equal, this implies that additional subtasks have been specified by the conference driver, and the routine proceeds to step 504. At step 504, the client sends a request for new image data if the parameters that have changed indicate that new image data has been generated. On the other hand, if only state parameters relating to brightness or contrast level, for example, are changed, then no new image data need be requested, because this change can be processed on the data already stored at the client. At step 505, the client state parameters are set equal to the updated server state parameters. At step 506, $\Delta t$ is set equal to zero.

What has just been described is an on-demand image transmission method. Unlike the existing conference systems, image transmission occurs only when needed, and therefore, the network utilization efficiency is greatly improved.

In an alternative embodiment, a "push" implementation is utilized. In the push implementation, state parameters are transmitted to the clients whenever they are changed. Also, new image data is transmitted if, as described above, the change in the state parameters required new server-side image processing.

In another alternative embodiment, all remote conference participants may have already had the copy of the same data set on each of their local disk. This may be the case for training or educational applications in which a standard set of data is utilized. In this case, no image data transmission is required over the network. Based on the state parameters maintained on the server, the conferencing software running on each participant's computer will generate the new image using the local copy of the data and local computing resources and will synchronize the image display. This embodiment is useful when the conference participants only have relatively-narrow bandwidth connection, such as a phone line, which is adequate to communicate the state parameters interactively, but not adequate for transmitting big data files, such as images, at rate allowing real time interaction. Updated state parameters in this embodiment may be transmitted to the clients either in a push implementation or a pull implementation.

As part of the preferred embodiment, any participant in a conference may request to become the driver. Upon approval from the current driver, the driver privilege may be switched to the requesting participant. The new driver will then have the full control of the image/data set under study, i.e., the ability to define new state parameters. The new driver, e.g., a surgeon, may fine tune the 3D model or other parameters to achieve the best view for his intended application.

The present invention may also be applied to multi-center trial studies, when constant communication of comprehensive information including images and data are needed between multiple participants. One example is a Magnetic Resonance Angiography (MRA) multi-center trial. In an MRA study, a 3D volumetric data set, comprised of a stack of 2D images, is acquired. This 3D volumetric data set is processed to extract the vascular structure, while minimizing the interference of other unwanted structures. In order to select the highest quality protocols and design the most effective trial, the participants need to view not only the acquisition protocol and the original 2D images, but also the processed 3D MRA images in detail.

The existing multi-center trial procedures face several challenges. First, in order to reach consensus on trial protocols, principle investigators from participating institutions may need to travel to different locations multiple times, making this process time consuming and expensive. Second, the current procedure of site selection, training, and trial monitoring require frequent travel by the trial monitors to various participating sites, making this process heavily dependent on the trial monitors' travel schedule and availability. Third, the current process calls for transferring of all the patient data/images to a centralized position, demanding significant amount of pre-work to modify studies headers and preserve patient privacy.

The present invention provides an optimized method for multi-center trial management using the teleradiology conferencing technology. This method is designed to optimize the workflow and management of various tasks, such as protocol selection, training/education, trial monitoring, and data management for expert reading.

The steps for future multi-center trial management using the present invention include:

1) Using the teleradiology conferencing techniques described herein to choose a trial protocol;
2) Subsequently using the training embodiment of the teleradiology conferencing techniques described herein to conduct interactive conferences hosted by the sites experienced in the selected protocols to provide training/education to other participating sites using the mechanism described in the above section;
3) Using the teleradiology conferencing techniques described herein to conduct interactive conferences between the trial monitor and individual participating sites to review images, in order to assure quality and compliance during trial process;
4) Using the teleradiology techniques described in our application, U.S. Ser. No. 09/434,088, and the present invention to allow an expert reader to remotely review, and interactively process if needed, 2D/3D image sets store at centralized or disparate locations, without physically transmitting the entire image sets; and
5) Reporting Expert reader will report blind read results using the integrated reporting tools provided by a system based on the present invention.

While the present invention has been described in its preferred embodiments, it is understood that the words which have been used are words of description, rather than limitation, and that changes may be made without departing from the true scope and spirit of the invention in its broader aspects. Thus, the scope of the present invention is defined by the claims that follow.

What we claim is:

1. A system for remote manipulation of image data over a telecommunications network, the system comprising:
   an image data storage library;
   an image processing server coupled to the telecommunications network and further coupled to the image data storage library; and
   a plurality of receiving stations coupled to the telecommunications network, each of the plurality of receiving stations having a memory for storing local copies of state parameters that keep track of the effect of image processing, the plurality of receiving stations including a first receiving station and a second receiving station, wherein the first receiving station transmits state parameters through the telecommunications network to the image processing server, and wherein the image processing server receives image data from the image data storage library and processes the image data in accordance with the received state parameters, and wherein the image processing server transmits processed image data through the telecommunications network to the first and second receiving stations and transmits the state parameters to the second receiving station to synchronize image display by the second receiving station to be consistent with image display by the first receiving station.

2. The system of claim 1 wherein at least one of the receiving stations transmits a request for processed image data through the telecommunications network and wherein the image processing server transmits processed image data to the receiving station through the telecommunications network in response to the request.

3. The system of claim 1 wherein the image processing server transmits processed imaged data to at least one receiving station upon the completion of the processing of image data.

4. The system of claim 1 wherein a first one of the plurality of receiving stations includes a user interface means for altering the local copy of state parameters and a means for transmitting the local copy of the state parameters, and wherein the first one of the plurality of receiving stations transmits a copy of the local copy of the state parameters through the telecommunications network to the image processing server.

5. The system of claim 1 wherein a first one of the plurality of receiving stations includes a user interface means for altering the local copy of state parameters and a means for transmitting the local copy of the state parameters, and wherein the first one of the plurality of receiving stations transmits a copy of the local copy of the state parameters through the telecommunications network to the image processing server and wherein at least one other of the plurality of receiving stations receives the state parameters through the telecommunications network from the image processing server and stores a local copy in the memory of the at least one other of the plurality of receiving stations.

6. The system of claim 5 wherein the at least one other receiving station transmits a request for processed image data through the telecommunications network and wherein the image processing server transmits processed image data to the receiving station through the telecommunications network in response to the request.

7. The system of claim 5 wherein the image processing server transmits processed imaged data to the at least one other receiving station upon the completion of the processing of image data.

8. The system of claim 4 further comprising means for authorizing only the first one of the plurality of receiving stations to alter and transmit the local copy of state parameters, and means for removing the authorization from the first one of the plurality of receiving stations and granting the authorization to another one of the plurality of receiving stations.

9. The system of claim 1 further comprising a display means coupled to a user input device, the user input device including a means for manipulating the movement of a cursor displayed on the display means and a means for causing text and graphics to be displayed on the display means, wherein the state parameters include parameters indicating the location of the cursor on the display means and the location and content of text and graphics on the display means.

10. The system of claim 1 wherein the image data are comprised of volumetric data.

11. A system for remote manipulation of image data using a telecommunications network, the system comprising:

an image data storage library;

an image processing server coupled to the telecommunications network and further coupled to the image data storage library; and a plurality of receiving stations coupled to the telecommunications network, the plurality of receiving stations including first and second receiving stations that participate in substantially concurrently viewing consistent images;

wherein the image processing server includes a first memory for storing a server set of state parameters, a server-side machine-readable medium, and a server-side processor that executes a first program stored in the server-side machine-readable medium, the first program causing the server-side processor to perform the steps of:

controlling the reception of an update set of state parameters over the telecommunications network from the first receiving station, the state parameters keeping track of the effect of image processing to synchronize displays of the first and second receiving stations such that an image being displayed by the second receiving station is consistent with an image being displayed by the first receiving station;

controlling the determination of whether the received update set of state parameters differs from the server set of state parameters in a manner which requires new processing of the image data;

controlling the processing of image data according to the update set of state parameters;

controlling the transmission the update set of state parameters from the image processing server to the second receiving station; and controlling the transmission of new image data from the image processing server to the first and second receiving stations if the update set of state parameters required processing of image data at the image processing server; and wherein the plurality of receiving stations include a second memory for storing a local set of state parameters, a client-side machine-readable medium, and a client-side processor that executes a second program stored in the client-side machine-readable medium, the second program causing the client-side processor to perform the steps of:

controlling the transmission of a request for new state parameters to the image processing server through the telecommunications network;

controlling the reception of state parameters from the image processing server over the telecommunications network;

controlling the determination of whether the received state parameters differ from the local set of state parameters and whether the received state parameters require non-local processing of image data; and controlling the transmission of a request for updated image data from the receiving station to the image processing server if a determination is made in the determining step that the received state parameters require non-local processing of image data.

12. The system of claim 11 wherein at least one of the plurality of receiving stations includes a user interface means for altering a set of state parameters stored in the memory and a transmission means coupled to the telecommunications network for transmitting the set of state parameters stored in the memory.

13. The system of claim 11 wherein at least one of the receiving stations transmits a request for processed image data through the telecommunications network and wherein the image processing server transmits processed image data to the receiving station through the telecommunications network in response to the request.

14. The system of claim 11 wherein the image processing server transmits processed imaged data to at least one receiving station upon the completion of the processing of image data.

15. A system for remote manipulation of image data using a telecommunications network, the system comprising:
   a communications server coupled to the telecommunications network;
   a plurality of receiving stations, the receiving stations including first and second receiving stations, the receiving stations including a first memory for storing a local set of state parameters keeping track of the effect of image processing, a first client-side machine-readable medium containing a pre-stored set of image data, a second client-side machine-readable medium, and a client-side processor that executes a program stored in the second machine-readable medium, the program causing the processor to perform the steps of:
   controlling the transmission of a request for new state parameters to the communication server through the telecommunications network;
   controlling the reception of state parameters from the first receiving station obtained from the communications server over the telecommunications network;
   controlling the determination of whether the received state parameters differ from the local set of state parameters; and
   controlling the processing of the pre-stored image data based on the received state parameters;
   wherein the communications server includes a second memory for storing a server set of state parameters, a server-side machine-readable medium, and a server-side processor that executes a second program stored in the third machine-readable medium, the second program causing the second processor to perform the steps of:
   controlling the reception by the communications server of an update set of state parameters over the telecommunications network; and
   controlling the transmission the update set of state parameters from the communications server to the second receiving station to synchronize a display of the second receiving station to display an image that is consistent with an image being displayed by the first receiving station.

16. The system of claim 15 wherein at least one of the plurality of receiving stations includes a user interface means for altering a set of state parameters stored in the memory and a transmission means coupled to the telecommunications network for transmitting the set of state parameters stored in the memory.

17. The system of claim 15 wherein at least one of the receiving stations processes image data stored in the local memory according to the received set of state parameters.

* * * * *

UNITED STATES PATENT AND TRADEMARK OFFICE
CERTIFICATE OF CORRECTION

PATENT NO. : 7,039,723 B2 Page 1 of 1
APPLICATION NO. : 09/945479
DATED : May 2, 2006
INVENTOR(S) : Hui Hu and Yi Sun It is certified that error appears in the above-identified patent and that said Letters Patent is hereby corrected as shown below:

On Title Page Item (73) under "Assignee", in column 1, lines 1-2, delete "HInnovation, Inc., Wauwatosa, WI (US)" and insert - - Vital Images, Inc., Minnetonka, MN (US) - -, therefor.

Signed and Sealed this

Fifth Day of September, 2006

JON W. DUDAS
*Director of the United States Patent and Trademark Office*